(12) United States Patent
Ohmi et al.

(10) Patent No.: US 6,622,543 B1
(45) Date of Patent: Sep. 23, 2003

(54) GAS DETECTION SENSOR

(75) Inventors: Tadahiro Ohmi, 1-17-301, Komegahukuro 2-chome, Aoba-ku, Sendai-shi, Miyagi 980-0813 (JP); Kouji Kawada, Osaka (JP); Nobukazu Ikeda, Osaka (JP); Akihiro Morimoto, Osaka (JP); Yukio Minami, Osaka (JP); Katunori Komehana, Osaka (JP); Teruo Honiden, Osaka (JP)

(73) Assignees: Fujikin Incorporated (JP); Tadahiro Ohmi (JP)

(*) Notice: Subject to any disclaimer, the term of this patent is extended or adjusted under 35 U.S.C. 154(b) by 0 days.

(21) Appl. No.: 09/979,039

(22) PCT Filed: Jun. 5, 2000

(86) PCT No.: PCT/JP00/03658
§ 371 (c)(1),
(2), (4) Date: Nov. 15, 2001

(87) PCT Pub. No.: WO01/94925
PCT Pub. Date: Dec. 13, 2001

(51) Int. Cl.[7] ............... G01N 25/32; G01N 27/16; G01N 27/00
(52) U.S. Cl. ............... 73/23.31; 73/25.05; 73/204.24; 73/25.01; 422/95; 204/258; 204/228.3
(58) Field of Search ............... 73/23.31, 25.01, 73/25.05, 204.24, 204.26; 422/95; 204/258, 228.3

(56) References Cited

U.S. PATENT DOCUMENTS

| | | | | |
|---|---|---|---|---|
| 3,592,055 A | * | 7/1971 | Dorman ............... | 73/188 |
| 4,298,574 A | * | 11/1981 | Bohl ............... | 422/97 |
| 4,774,833 A | * | 10/1988 | Weibler et al. ............... | 73/118.2 |
| 4,782,708 A | * | 11/1988 | Harrington et al. ............... | 73/861.05 |
| 5,515,714 A | * | 5/1996 | Sultan et al. ............... | 73/25.01 |
| 5,616,850 A | * | 4/1997 | Sage ............... | 73/23.31 |
| 5,703,288 A | * | 12/1997 | Horiguchi et al. ............... | 73/204.26 |
| 5,804,703 A | * | 9/1998 | Wind et al. ............... | 73/25.01 |
| 5,841,021 A | * | 11/1998 | De Castro et al. ............... | 73/23.2 |
| 5,880,354 A | * | 3/1999 | Newman et al. ............... | 73/25.01 |
| 5,948,965 A | * | 9/1999 | Upchurch et al. ............... | 73/23.31 |
| 6,009,742 A | * | 1/2000 | Balko ............... | 73/23.31 |
| 6,040,579 A | * | 3/2000 | Munch et al. ............... | 250/344 |
| 6,101,872 A | * | 8/2000 | Zechnall et al. ............... | 73/204.26 |
| 6,279,394 B1 | * | 8/2001 | Svoboda et al. ............... | 73/204.26 |

FOREIGN PATENT DOCUMENTS

| | | |
|---|---|---|
| JP | 57-039342 A | 3/1982 |
| JP | 11-030602 A | 2/1999 |
| JP | 2000-171422 A | 6/2000 |

\* cited by examiner

Primary Examiner—Helen Kwok
Assistant Examiner—David J. Wiggins
(74) Attorney, Agent, or Firm—Griffin & Szipl, P.C.

(57) ABSTRACT

A gas detection sensor permits precise measurement of the concentration of flammable gas in a detection or subject gas and the concentration of oxygen in a detection gas containing flammable gases. In the sensor, the heating of the sensor by contact catalytic reaction of flammable gas gives off a detection signal of the flammable gas. The gas detection sensor has a first detection sensor including a diaphragm having a platinum coat on a side which the flowing detection gas comes in contact with, and a thermocouple having respective ends of two different metals placed close to each other and fixed on the side of the diaphragm not coming in contact with the flowing detection gas and which is heated by the contact catalytic reaction of flammable gas. A second detection sensor similar to the first detection sensor detects the temperature of the flowing detection gas.

10 Claims, 10 Drawing Sheets

GAS DETECTION SENSOR

FIELD OF THE INVENTION

The present invention relates to improvements in a detection sensor for flammable gases and oxygen gas in flammable gases. More particularly, the present invention relates to the sensor for such uses as in securing and ensuring the safety of a variety of production equipment and facilities and detection of hydrogen gas in pure water for manufacturing semiconductors and hydrogen gas in gases for manufacturing semiconductors.

BACKGROUND OF THE INVENTION

Among the detection sensors for flammable gases that have been used widely are the contact catalytic reaction type (or the contact combustion type) gas detection sensor, semiconductor type gas detection sensor and thermal conductivity type gas detection sensor. Of those types, the contact catalytic reaction type gas detection sensor has found wide uses for detection of such gases as hydrogen gas because of its long service life and reliability.

FIG. 10 shows a partially broken way view of an example of the sensor element A of the prior art contact catalytic reaction type gas detection sensor. This sensor element A includes a coil B of platinum wire some 20 $\mu$m in diameter with which a mixture of a binder and alumina or silica alumina to be a catalyst support C is sintered, with a catalyst D like platinum supported therein.

The aforesaid sensor element A is incorporated in a bridge circuit for detection of gas concentration. That is, a bridge circuit is formed, as shown in FIG. 11, with the sensor element A and a temperature compensation element Ao made by sintering an inert substance. A specific voltage is applied to the sensor element A to raise before hand the temperature to not lower than some 250° C. If a flammable gas like hydrogen gas comes in contact with the preheated sensor element A, the gas will undergo a contact catalytic reaction by the catalytic action of catalyst D and the sensor element A will be heated. That increases the electrical resistance of the sensor element A to break the equilibrium in the bridge circuit and to cause an electric potential difference. As a result, an indicator E turns. The extent of the turn of the indicator shows the heating value of the sensor element A, that is, the concentration of the flammable gas within the detection gas or subject gas under test.

The sensor element A as shown in FIG. 10 has such advantages as (a) high selectivity for flammable gases, (b) hardly influenced by the co-existing $H_2O$ and (c) suitable for measurement of gas concentration close to the lower limit of explosion (in the case of hydrogen gas, 1 to 4%).

However, the problem with the sensor element A as shown in FIG. 10 is that the temperature of the sensor element A has to be maintained at not lower than 250° C. and that the working temperature further rises in detection of the flammable gas concentration. That could ignite the flammable gas. To ensure the safety, the sensor element A has to be made explosion-free by covering the sensor element A with such as a wire netting with a mesh of some 200 or sintered metal. In other words, the sensor element A as shown in FIG. 10 has a serious safety problem.

It is also noted that this type of sensor element A is so formed that catalyst D is supported within the catalyst support C as mentioned, and has a basic problem about the stability of catalytic activity. Especially, the effects on the catalyst in the sinter material by the burning of the flammable gas and the effects on the catalytic activity of carbon coming from incomplete combustion of the flammable gas haven not been elucidated well yet. Few studies are reported in which this type of the sensor element A is used for detection of a flammable gas which is present in small quantities in highly concentrated $H_2O$ or $O_2$.

Another problem is that it is difficult to clean the inside of the catalyst support C of this kind of the sensor element A. For this reason, the sensor element A can not be used in the semiconductor manufacturing process where a high degree of cleanliness is required.

As set forth above, the application of the contact catalytic reaction type flammable gas detection sensor A for detection of a flammable gas present in small amounts in highly concentrated $H_2O$ or $O_2$ presents problems with regard to reliability and the like. It is also the case with the use of the semiconductor type flammable gas detection sensor and the thermal conductivity type flammable gas detection sensor. Furthermore, while it is possible to use this kind of the sensor element A as sensor for detection of oxygen in the flammable gases in principle, it has not been put to practical use because of the aforesaid problems like reliability, and few application studies have been reported.

In other words, the prior art flammable gas detection sensor A of the contact catalytic reaction type drops substantially with lapse of time in catalytic activity, that is, $H_2$ gas detection sensitivity. For reasons of poor reliability, the sensor element A can hardly be applied for such uses as detection of the concentration of unreacted hydrogen gas in the moisture take-out line of the moisture generating reactor for semiconductor manufacturing facilities. The same is the case with the aforesaid semiconductor type sensor for detection of hydrogen gas and the thermal conductivity type sensor for detection of hydrogen gas, which has been confirmed in experiments.

In the moisture generating reactor for semiconductor manufacturing facilities, it can happen that moisture is generated with excessive supply of hydrogen gas. In such a case, it is necessary to detect the concentration of unreacted oxygen gas in the generated moisture containing hydrogen in the moisture take-out line. The prior art sensor element A can not be used in such cases.

Meanwhile, the applicants of the present application developed a flammable gas detector as shown in FIG. 12 that solved the problems with the prior art contact catalytic reaction type sensor element A for detection of flammable gases and disclosed the same in unexamined Japanese patent application No. 9-186383.

This flammable gas detector is composed of a flammable gas detection sensor 20 and a detector unit 30. The flammable gas detection sensor 20 is formed of a first detection sensor 21 provided with a platinum coating catalyst, a second detection sensor 22 to detect the temperature of the detection gas (the gas to be detected) or subject gas under test and a sensor holder 23.

The detector unit 30 includes a first temperature detector 31 to detect the temperature signal from the first detection sensor 21, a second temperature detector 32 to detect the temperature signal from the second detection sensor 22, a first temperature display 33 and second temperature display 34 to display the temperatures detected by the aforesaid two temperature detectors respectively, a temperature difference detector 35 to detect the difference between the detected temperatures and a temperature difference display 36 to display the temperature difference from the temperature difference detector 35.

The flammable gas detection sensor 20 is placed in a T-shaped branch pipe 39 with the sensor holder 23 fitted in air-tight and with the two sensor elements 21, 22 held in a gas feeder pipe 37 as shown in FIG. 13. The T-shaped branch pipe 39 is provided with explosion proof metal meshes 38 in gas feeder pipe 37.

The flammable gas detector shown in FIG. 12 and FIG. 13 is excellent in responsiveness and gas concentration detection accuracy, and can correct the detected value without difficulty when the flow rate of the detection gas changes. Another practical advantage is that the change with lapse of years in detection sensitivity is relatively small.

But this flammable gas detector has a number of problems yet to be solved. Among the problems requiring urgent solution are contamination of the high-purity gas flowing through the pipe, the reliability of detection precision and safety.

To be specific, the first detection sensor 21 and the second detection sensor 22 to be placed in the high-purity gas are thermocouples, and the outer surface of the first detection sensor 21 to be heated by the contact catalytic reaction of flammable gas is coated with a platinum catalyst film via a barrier coat like TiN.

However, the adhesion strength between the metal, for example, chromel-alumel, forming the thermocouple and the barrier coat like TiN undergoes a change relatively fast with lapse of years. As a result, the platinum coat on the first detection sensor 21 could fall off, contaminating the high-purity gas. In other cases, partial peeling off of the platinum coat could reduce the catalytic reactivity.

The detection sensors may be formed of platinum. An example is a gas detection sensor that has the thermocouple of the first detection sensor 21 made of noble metals like platinum and rhodium and that has the second detection sensor 22—to detect the temperature of the fluid—also made of platinum and rhodium with the outer surface coated with a barrier coat like TiN. In this case, there is no fear that the barrier coat will come off with lapse of years.

However, the thermocouple of noble metals would be relatively expensive and present problems with mechanical strength and machining, which would make it difficult to put it to practical use.

The present invention address the following problems with the gas detection sensor of the type shown in FIG. 12: (a) the thermocouple made of base metals is liable to deteriorate in adhesion between the platinum coat and the thermocouple forming material with passage of years, with peeled off platinum coat contaminating the high-purity gas and reducing catalytic reactivity, (b) the thermocouple made of noble metals is expensive to manufacture, and (c), in the latter case, difficulty in machining and relatively low mechanical strength, making it difficult to reduce manufacturing costs.

It is accordingly an object of this invention to provide a gas detection sensor that is free from contaminating the high-purity gas and from changing with passage of time in detection precision, yet is excellent in safety and relatively inexpensive to manufacture.

SUMMARY OF THE INVENTION

The inventors have been engaged in developing reactors for generating moisture for many years, and in the course of the research and development they have succeeded in stabilizing the platinum coat formed on the inside wall of the reactor made of stainless steel, that is, preventing the catalytic performance from changing with time.

Then, the inventors have noticed that it is possible to build a flammable gas sensor with little deterioration in catalytic performance and with high reliability and safety at low costs if the technique for forming a platinum catalytic layer in the reactor for generating moisture is applied to a flammable gas detector.

On the basis of that finding, the inventors, thinking that the change in output caused by a change in the temperature of the thermocouple should be a factor in detecting the flammable gas concentrations, tested various characteristics of thermocouples of different types and studied the results in detail.

The present invention was made through such a process. The invention comprises a gas detection sensor wherein flammable gas detection signals are issued by the heating of the sensor caused by the contact catalytic reaction with the flammable gas. The gas detection sensor includes a first detection sensor having a diaphragm with a platinum coat on the gas contact surface coming in contact with the flowing detection gas, and a thermocouple having the one ends of two metal pieces of different kinds placed close to each other and fixed on the side of the diaphragm not coming in contact with gas—the reverse of the side that comes in contact with the detection gas and which is heated by the contact catalytic reaction of flammable gas—; and a second detection sensor which includes a diaphragm coming in contact with the flowing detection gas and a thermocouple having the one ends of two metal pieces of different kinds placed close to each other and fixed on the side of the diaphragm not coming in contact with gas—the reverse of the side that comes in contact with the detection gas—and which detects the temperature of the flowing detection gas.

An object of the invention is to provide a gas detection sensor wherein detection signals for oxygen gas in the flammable detection gas are issued by the heating of the sensor owing to contact catalytic reaction with the flammable gas. This gas detection sensor comprises: a first detection sensor which includes a diaphragm having a platinum coat on the gas contact surface coming in contact with the flowing detection gas and a thermocouple having the one ends of two metal pieces of different kinds placed close to each other and fixed on the side of the diaphragm not coming in contact with gas—the reverse of the side that comes in contact with the detection gas—and which is heated by the contact catalytic reaction of flammable gas; and a second detection sensor which includes a diaphragm coming in contact with the flowing detection gas and a thermocouple having the one ends of two metal pieces of different kinds placed close to each other and fixed on the side of the diaphragm not coming in contact with gas—the reverse of the side that comes in contact with the detection gas—and which detects the temperature of the flowing detection gas.

A further object of the invention is to provide a sensor as described above wherein the diaphragms in the first detection sensor and the second detection sensor are made of stainless steel and wherein a barrier coat is formed on the sides of the two diaphragms that come in contact with the gas.

According to the invention, the barrier coat is formed of an oxide or nitride and/or each thermocouple may be made of chromel-alumel.

A further object of the invention is to provide a sensor as described above wherein the diaphragms of the first detection sensor and the second detection sensor are fit into the detection sensor insertion ports of the stainless steel sensor block, with the gas-contact surface of the diaphragm facing the gas passage and with the inserting ports sealed airtight with the respective diaphragms. The stainless steel sensor block is each provided with an inlet and an outlet for detection gas, a gas passage through which the inlet communicates with the outlet and the first detection sensor inserting port and the second detection sensor inserting port which communicate with the gas passage.

Figure 1:
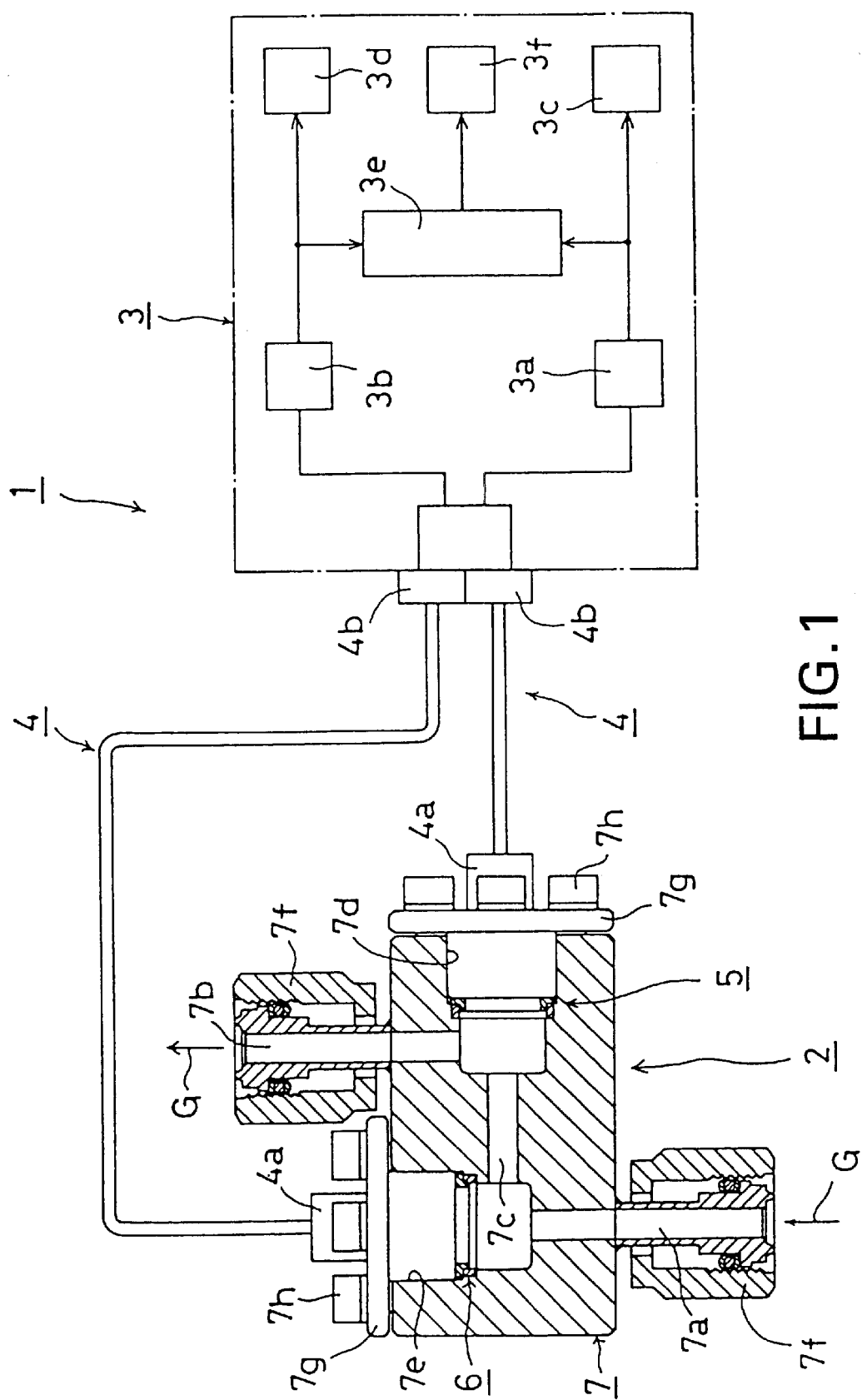
FIG. 1 is a block diagram of a flammable gas detection sensor of the present invention.

List of Reference Numerals
A sensor element
B coil
C catalyst support
D catalyst
Ao temperature compensation element
E indicator
$A_1$ for thermocouple
$A_2$ metal for thermocouple
G gas sample
1 flammable gas detector
2 detection sensor
3 detector unit
3a first temperature detector
3b second temperature detector
3c first temperature display
3d second temperature display
3e temperature difference detector
3f temperature difference display
4 connection cable
4a connector
4b connector
5 first detection sensor
5a diaphragm base
5b diaphragm
5c barrier coat
5d platinum coat
5e thermocouple
5e' sheath
5e" annulus
6 second detection sensor
6a stainless steel
6b diaphragm
6c barrier coat
6e thermocouple
6e' sheath
6e" annulus
7 sensor block
7a gas inlet
7b gas outlet
7c gas passage
7d first detection sensor inserting port
7e second detection sensor inserting port
7f metal fittings for pipe connection
7g metal fitting for mounting the sensor
7h bolt for mounting the sensor
8 thermocouple holder
8a barrier coat
8b platinum coat
9 seal ring
10 potentiometer

DESCRIPTION OF THE PREFERRED EMBODIMENTS

Now, the embodiments of the present invention will be described with reference to the drawings.

Figure 2:
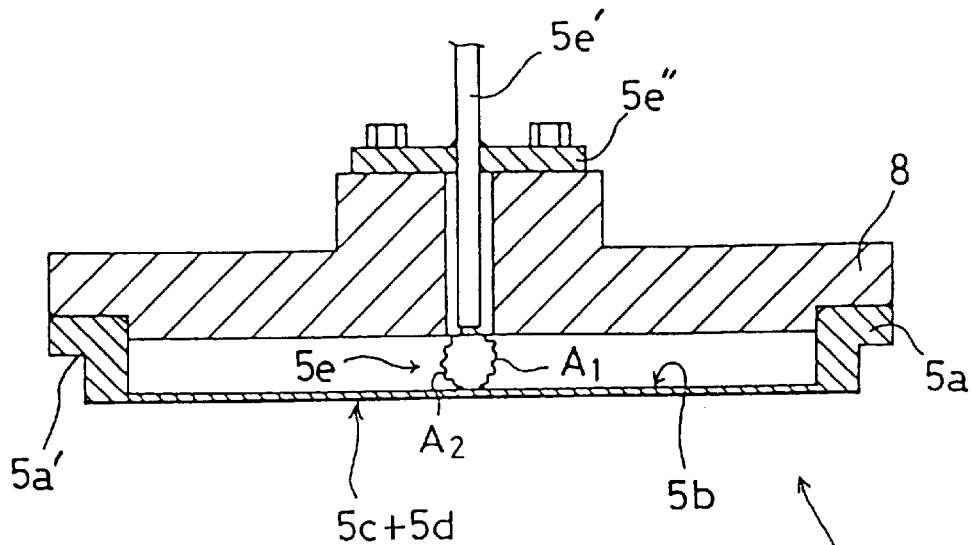
FIG. 2 is a sectional view of the first detection sensor.
Figure 3:
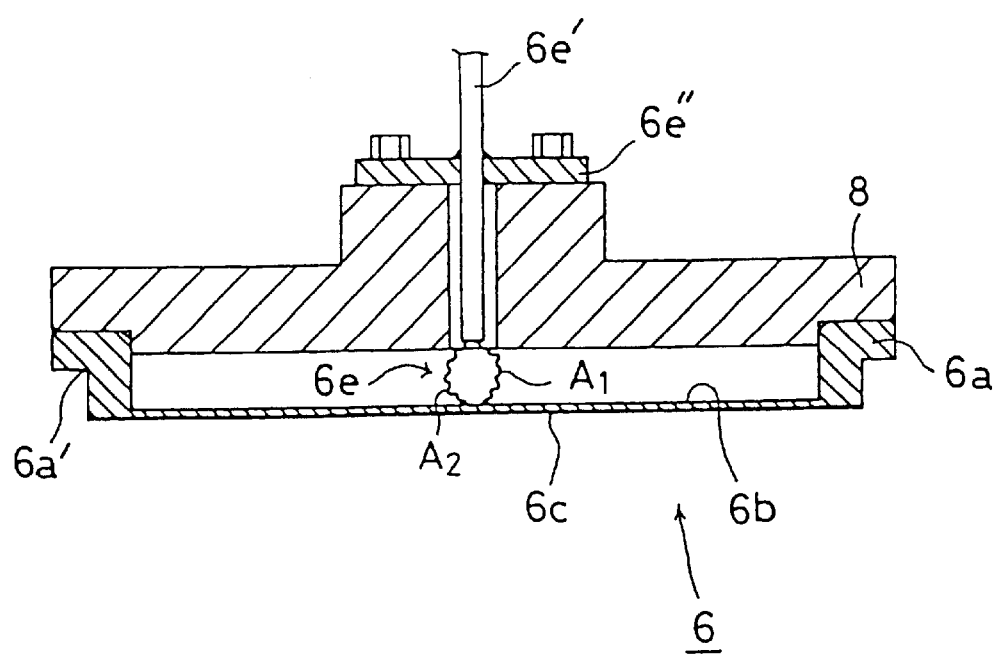
FIG. 3 is a sectional view of the second detection sensor.
Figure 4:
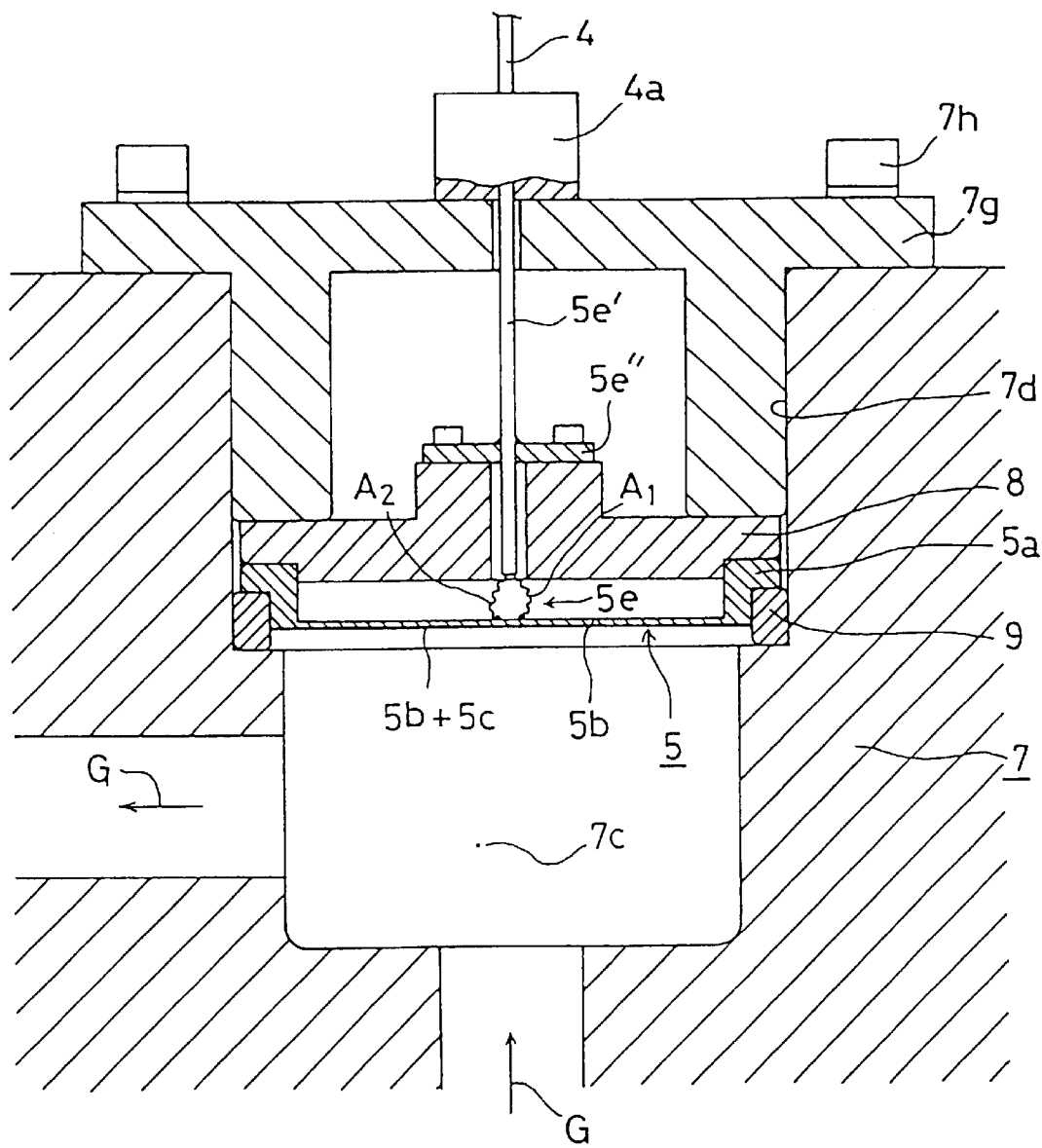
FIG. 4 is a sectional view of the first detection sensor fit into the sensor block.
Figure 5:
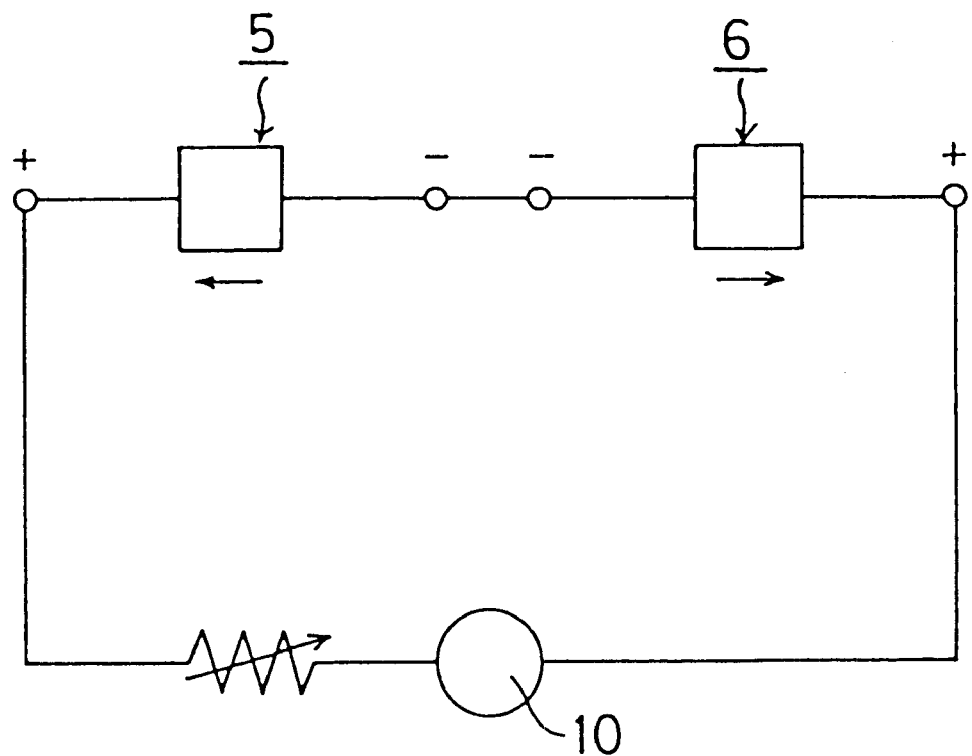
FIG. 5 is a block diagram showing another embodiment of the detector body of the flammable gas detector.

FIG. 1 is a block diagram of a flammable gas detector in which a flammable gas detection sensor 2 according to the present invention is applied. FIG. 2 is a sectional view of the first detection sensor 5. FIG. 3 is a sectional view of the second detection sensor 6. And FIG. 4 is an enlarged partially sectional view of the first detection sensor 5 fit into the sensor block 7.

Referring to FIG. 1, the flammable gas detector 1 according to the present invention comprises the flammable gas detection sensor 2, the detector unit 3 and the connection cables 4 that connect the detection sensor 2 and the detector unit 3.

The flammable gas detection sensor 2 includes the first detection sensor 5 provided with a platinum coat, the second detection sensor 6 for detecting the temperature of the gas to be detected and the sensor block 7.

The sensor block 7 in the shape of a block is made of stainless steel under JIS designation SUS316L and has the flammable gas inlet 7a, the gas outlet 7b, the gas passage 7c, the first detection sensor inserting port 7d, the second detection sensor inserting port 7e and others. In FIG. 1, the numeral 7f indicates metal fittings for pipe connection, the numeral 7g metal fittings for mounting the sensors, and 7h bolts for mounting the sensors.

The detector unit 3 includes the first temperature detector 3a to detect the temperature signal from the first detection sensor 5, second temperature detector 3b to detect the temperature signal from the second detection sensor 6, the first temperature display 3c and the second temperature display 3d that display the detected temperatures from the two detectors respectively, the temperature difference detector 3e to detect the difference between the two detected temperatures, and the temperature difference display 3f to display the temperature difference from the temperature difference detector 3e.

The connection cables 4 have each detachable connectors 4a, 4b at the ends respectively and electrically connect the flammable gas detection sensor 2 and the detector unit 3.

The embodiment shown in FIG. 1 has the first temperature display 3c and the second temperature display 3d provided in the detector unit 3 which display the detected temperatures of the two sensors 5, 6 respectively. But that is not restrictive. The detector unit 3 may be provided with only the display 3f to show the temperature difference (that is, the concentration of flammable gas). Also, the temperature difference display 3f may be provided with a flammable gas concentration alarm (not shown). The detector unit 3 may be arranged in any form.

The first detection sensor 5 comprises, as shown in FIG. 2, the diaphragm base 5a made of stainless steel under JIS designation SUS316L, the diaphragm 5b molded integrally with the diaphragm base 5a, the barrier coat 5c formed on the gas-contact surface (outside surface) of the diaphragm 5b, the platinum coat 5d formed on the outside surface of the barrier coat 5c and the thermocouple 5e made of two different metals whose respective one ends are put close to each other and fixed on the surface (reverse side) of the diaphragm 5b not coming in contact with the gas.

In FIG. 2, the numeral 8 is a thermocouple holder that holds and fixes the sheath 5e' of the thermocouple 5e via the annulus 5e''.

The diaphragm base 5a is made of stainless steel under JIS designation SUS316L and is ring-formed in shape with a shoulder 5a' formed around the outer circumferential surface for a seal ring (not shown).

The diaphragm 5b is formed integrally with the diaphragm base 5a. The diaphragm 5b is originally some 1 mm thick and then polished as by lapping to a thickness of some 0.1 to 0.3 mm with an inside diameter of some 10 to 20 mm.

The barrier coat 5c is formed of TiN some 2 $\mu$m thick on the gas-contact surface of the diaphragm 5b.

In forming the barrier coat 5c, the outside surface (gas-contact surface) of the diaphragm 5b is subjected to a suitable surface treatment to remove a metal oxide layer or passive state film naturally formed on the surface of stainless steel. Then, a TiN barrier coat 5c is formed. In the present embodiment, a TiN film some 2 $\mu$m thick is formed by the ion plating technique.

The materials suitable for the barrier coat 5c includes nitride film like TiC, TiCN and TiAlN as well as TiN and oxide film like $Cr_2O_3$ and $SiO_2$. The thickness of the barrier coat 5c is preferably 0.1 to 5 $\mu$m. A thickness of not larger than 0.1 $\mu$m is not effective as barrier, while if the thickness exceeds 5 $\mu$m, it will take long to form a barrier coat and, in addition, the difference in expansion coefficient could cause the barrier coat to peel off or other problems when the film is heated.

Other methods of forming a barrier coat 5c than the ion plating technique may used. They include the physical vapor deposition (PVD) such as ion sputtering and vacuum deposition, chemical vapor deposition (CVD), also hot press method and flame spray coating.

The platinum coat 5d provided on the gas-contact surface of the diaphragm 5b of the first detection sensor 5 is a platinum coat some 0.2 $\mu$m thick formed on the barrier coat 5c. After the barrier coat 5c is formed, the platinum coat 8b is formed thereon. In the present embodiment, a platinum coat 5d some 0.2 $\mu$m thick is formed by the ion plating technique. The thickness of the platinum coat 5d is preferably 0.1 $\mu$m to 3 $\mu$m. A coating not thicker than 0.1 $\mu$m could not remain catalytically active for a long time. On the other hand, a coating thicker than 3 $\mu$m would increase the cost of forming the platinum coat 5d and would make little difference in catalytic activity and service life. Besides, a thicker coat could peel off when heated because of difference in expansion coefficient.

A platinum coating 5d may be formed not only by the ion plating technique but also ion sputtering, vacuum deposition, chemical vapor deposition and hot press. Platinum plating is also possible in case the barrier coat 13a is made of an electric conductive material such as TiN.

The thermocouple 5e is formed of two different kinds of metals A1, A2. The one ends of two metals $A_1$, $A_2$ are put close to each other—some 0.1 to 0.2 mm apart from each other—and fixed on the reverse side (not the gas-contact side) of the diaphragm 5b. The respective other ends of the two metals $A_1$, $A_2$ are drawn out through protection of the sheath 5e'.

In the present embodiment, it is noted that the thermocouple 5e is a base metal type alumel-chromel thermocouple 5e.

The thermocouple holder 8 is to hold and fix the thermocouple 5e. It is so designed that the sheath 5e' of the thermocouple 5e is held and clamped by fastening to the thermocouple holder 8 the annulus 5e' provided on the sheath 5e' of the thermocouple 5e.

Needless to say, the thermocouple holder 8 may be of any construction, as long as the holder 8 can hold and clamp the sheath 5e' of the thermocouple 5e.

The second detection sensor 6 is exactly identical with the first detection sensor 5 except that no platinum coat 5d is coated as shown in FIG. 3. In FIG. 3, the numeral 6a indicates a diaphragm base made of stainless steel (JIS designation SUS316L), the numeral 6b a diaphragm, the numeral 6c a barrier coat, the numeral 6e a thermocouple, the numeral 6e' a sheath, and the numeral 6e'' an annulus. The diaphragm 6b, barrier coat 6c, thermocouple 6e and others are exactly the same as those in the first detection sensor 5.

The diaphragm base 5a and diaphragm 5b and also the diaphragm base 6a and diaphragm 6b shown in FIG. 2 and FIG. 3 are integrally formed respectively. Instead, the diaphragm base 5a and diaphragm 5b and also the diaphragm base 6a and diaphragm 6b are each formed separately and put together as by welding.

In this embodiment shown in FIG. 2 and FIG. 3, it is so arranged that the diaphragm bases 5a, 6a and thermocouple holder 8 are provided. Needless to say, the diaphragm bases 5a, 6a and thermocouple holder 8 may be dropped as long as the diaphragms 5b, 6b can be inserted and fixed airtight in the sensor inserting ports 7d, 7e in the sensor block 7 and the thermocouples 5e, 6e can be firmly held and clamped.

Furthermore, the thermocouples 5e, 6e shown in FIG. 2 and FIG. 3 are base metal type chromel $A_1$-alumel $A_2$ (CA) thermocouples. Needless to say, thermocouples of other types may be used, including copper-constantan (CC) type, and iron-constantan (CI) type.

In the present embodiment, the sensor block 7 is formed in the shape of a block as shown in FIG. 1 and the first detection sensor 5 and the second detection sensor 6 are positioned in such a way as to form a right angle with each other wherein the detection gas G may come in contact with the second detection sensor 6 first and then with the first detection sensor 5. Instead, it may be so arranged that the detection gas G may first come in contact with the first detection sensor 5 and then with the second detection sensor 6.

In the present embodiment as shown in FIG. 1, furthermore, the first detection sensors 5, 6 are so positioned that the flow of the detection gas G crushes against the two sensors 5, 6. Needless to say, the two sensors 5, 6 may be lined up so that the detection gas G may flow along the gas-contact surfaces of the respective diaphragms 5b, 6b.

FIG. 4 is an enlarged partially sectional view of the first detection sensor 5 fit into the sensor block 7. In FIG. 4, the numeral 9 is a seal ring, the numeral 7g a metal fitting for fixing the sensor and the numeral 7h a bolt for fixing the sensor. The first detection sensor 5 is fit into the first detection sensor inserting port 7d of the sensor block 7 with the seal ring 9 placed around the sensor 5 inside the port 7d. Pressed from above by the metal fitting 7g for fixing the sensor, the first detection sensor 5 moves in until the gas-contact surface—the outside surface with the platinum coat 5d formed thereon—is exposed to the gas passage 7c. The first detection sensor 5 is fixed to the sensor block 7 with the first detection sensor inserting port 7d being maintained in an airtight state.

(Operation of the flammable gas detector)

The operation of the flammable gas detector 1 according to the present invention will be explained.

Referring to FIG. 1, the detection gas G that flows into the sensor block 7 from the gas inlet 7a first comes in contact with the diaphragm 6b of the second detection sensor 6 and then flows toward the first detection sensor 5.

The diaphragm 6b of the second detection sensor 6 is heated to about the same temperature as that of the detection gas G through the barrier coat 6c. That is, the temperature of the detection gas G is detected by the thermocouple 6e and input to the second temperature detector 3b.

It is noted that the diaphragm 6b and 6c are very thin and small in area with a diameter of some 10 to 20 mm. Therefore, the responsiveness to gas temperature detection by the thermocouple 6e is very high, which will be described later.

Another feature is that the gas-contact surface of the diaphragm 6b of the second detection sensor 6 is covered with the barrier coat 6c. Therefore, even if the detection gas G contains flammable gases like H2, there will arise no reaction heating by the so-called contact catalytic activity. As a result, the second detection sensor 6 always indicates the temperature of the detection gas G.

Furthermore, the barrier coat 6c effectively prevents what is called the metal dusting into the detection gas G from the diaphragm 6b and also perfectly prevents the catalytic action of the stainless steel forming the diaphragm 6b.

Meanwhile, the detection gas G that has passed through the second detection sensor 6 flows on toward the first detection sensor 5 and comes in contact with the gas-contact surface of diaphragm 5b.

The gas-contact surface of the diaphragm 5b of the first detection sensor 5 is provided with the platinum coat 5d as mentioned above. If the detection gas G contains flammable gases like $H_2$, the catalytic action of the platinum coat 5d will activate H2, causing a so-called contact catalytic reaction and heating the diaphragm 5b.

The diaphragm 5b is very thin—some 0.2 mm thick, and therefore, the heat from the contact catalytic reaction is immediately detected by the thermocouple 5e and input into the first temperature detector 3a.

The difference between the detected value of the first temperature detector 3a and that of the second temperature detector 3b is detected by the temperature difference detector 3e. From the difference therebetween, the concentration of flammable gas in the detection gas is found and displayed on the temperature difference display (flammable gas concentration display) 3f.

In the embodiment shown in FIG. 1, it is so configured that the outputs of the thermocouples 5e, 6e of the first detection sensor 5 and the second detection sensor 6 are input into the first temperature detector 3a and second temperature detector 3b of the detector unit 3 respectively. There, the temperature difference detector 3e detects the temperature difference between the two detectors 3a, 3b and converts the temperature difference into the concentration of flammable gas. However, the detector unit 3 may be of any construction. For example, the thermocouple output of the first detection sensor 5 and the output of the second detection sensor 6 may be connected in reverse polarity so that the output difference between the two first detection sensors 5, 6 may be read out on the potentiometer 10 and the reading of the potentiometer 10 may be directly converted into the concentration of flammable gas in the detection gas G.

EXAMPLE 1

Figure 6:
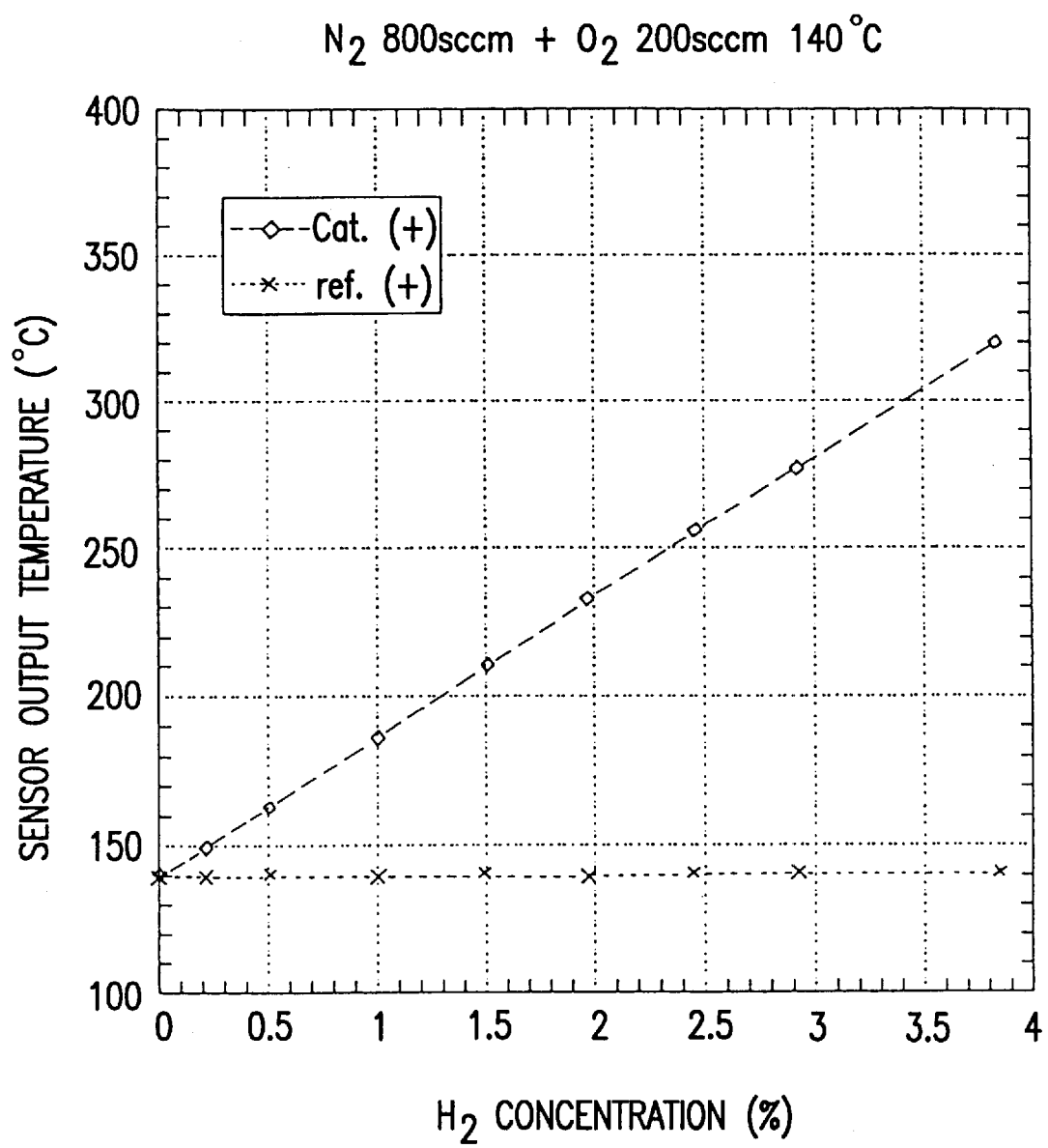
FIG. 6 is an example plot of sensor output temperature versus $H_2$ concentration of detection sensor.
Figure 7:
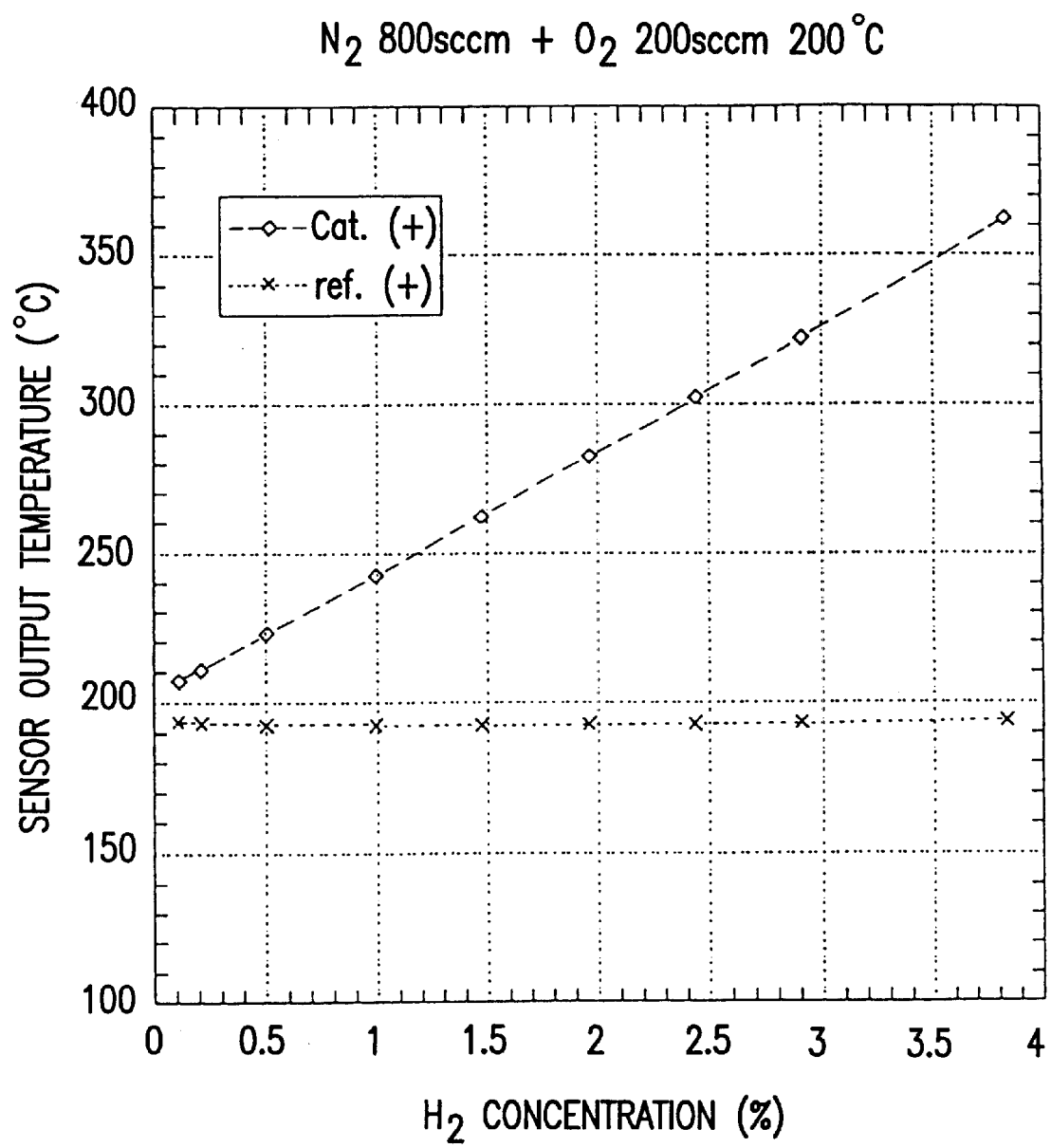
FIG. 7 is an example plot of sensor output temperature versus $H_2$ concentration of detection sensor.

FIG. 6 and FIG. 7 show the relationship between the $H_2$ concentrations in $O_2$-contained gas and the temperatures detected by the first detection sensor 5 and the second detection sensor 6 in an actual measurement experiment.

EXAMPLE 2

Figure 8:
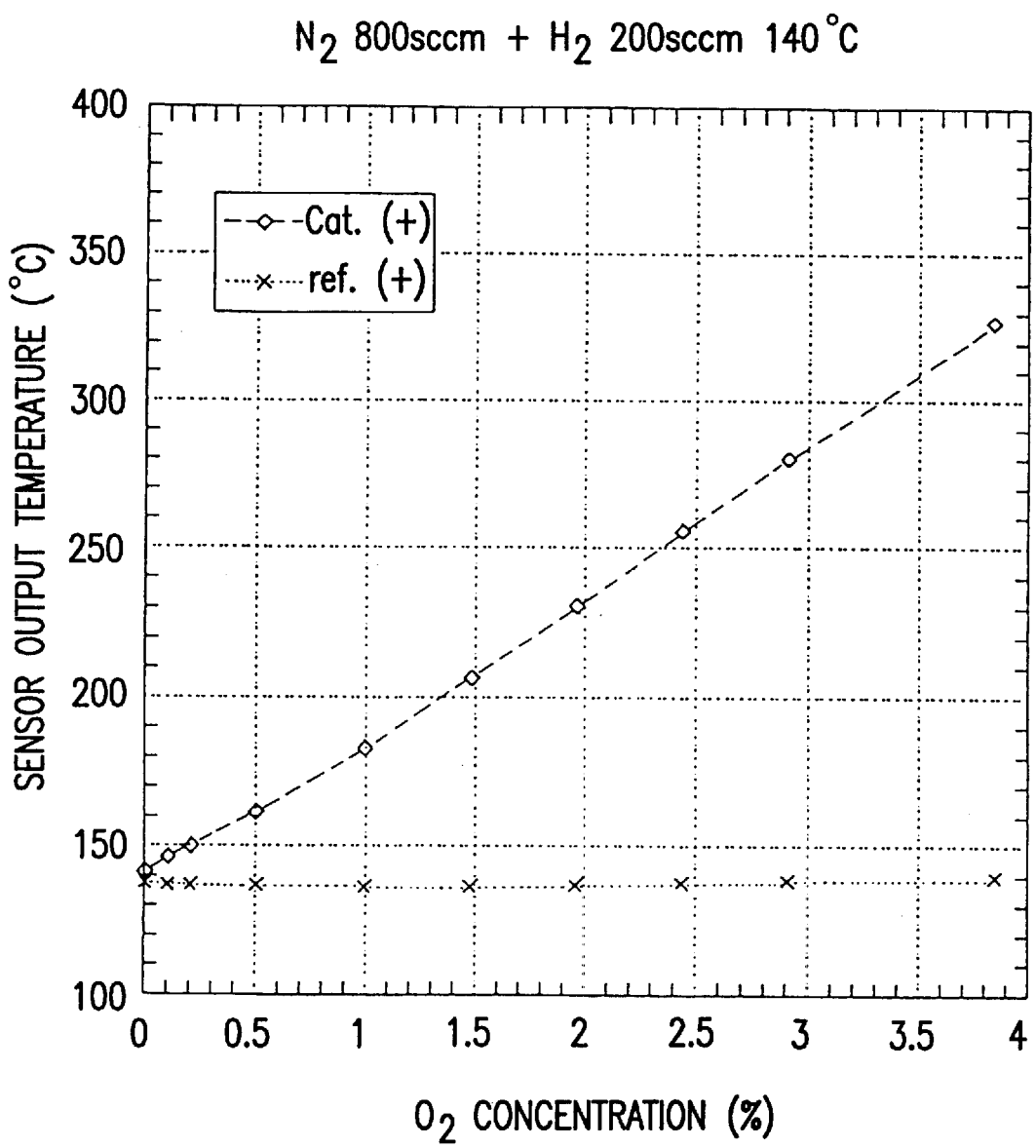
FIG. 8 is an example plot of sensor output temperature versus $O_2$ concentration of detection sensor.

FIG. 8 shows the relationship between the $O_2$ concentrations in $H_2$-contained gas and the temperatures detected by the first detection sensor 5 and the second detection sensor 6 in an actual measurement experiment.

In the first example and the second example, the first detection sensor 5 used in the experiments is made of stainless steel under JIS designation SUS316L, with the diaphragm 5b 0.2 mm in thickness, 20 mm in diameter, with the barrier coat 5c of TiN film 2.0 $\mu$m in thickness, with the platinum coat 5d 0.2 $\mu$m in thickness, with the thermocouple 5e of the alumel-chromel type, with the chromel tip and alumel tip held apart 0.2 mm from each other and fixed on the diaphragm 5b.

The second detection sensor 6 is the same as the first detection sensor 5 except that only the platinum coat 5d is absent.

As is evident from FIGS. 6 to 8, the temperature detected by the first detection sensor 5 is directly proportional with the concentration of $H_2$ or $O_2$. It is shown that from the difference (temperature difference) between the outputs from the detection sensors 5, 6, it is possible to detect the concentration of $H_2$ or $O_2$ in the detection gas G.

EXAMPLE 3

Figure 9:
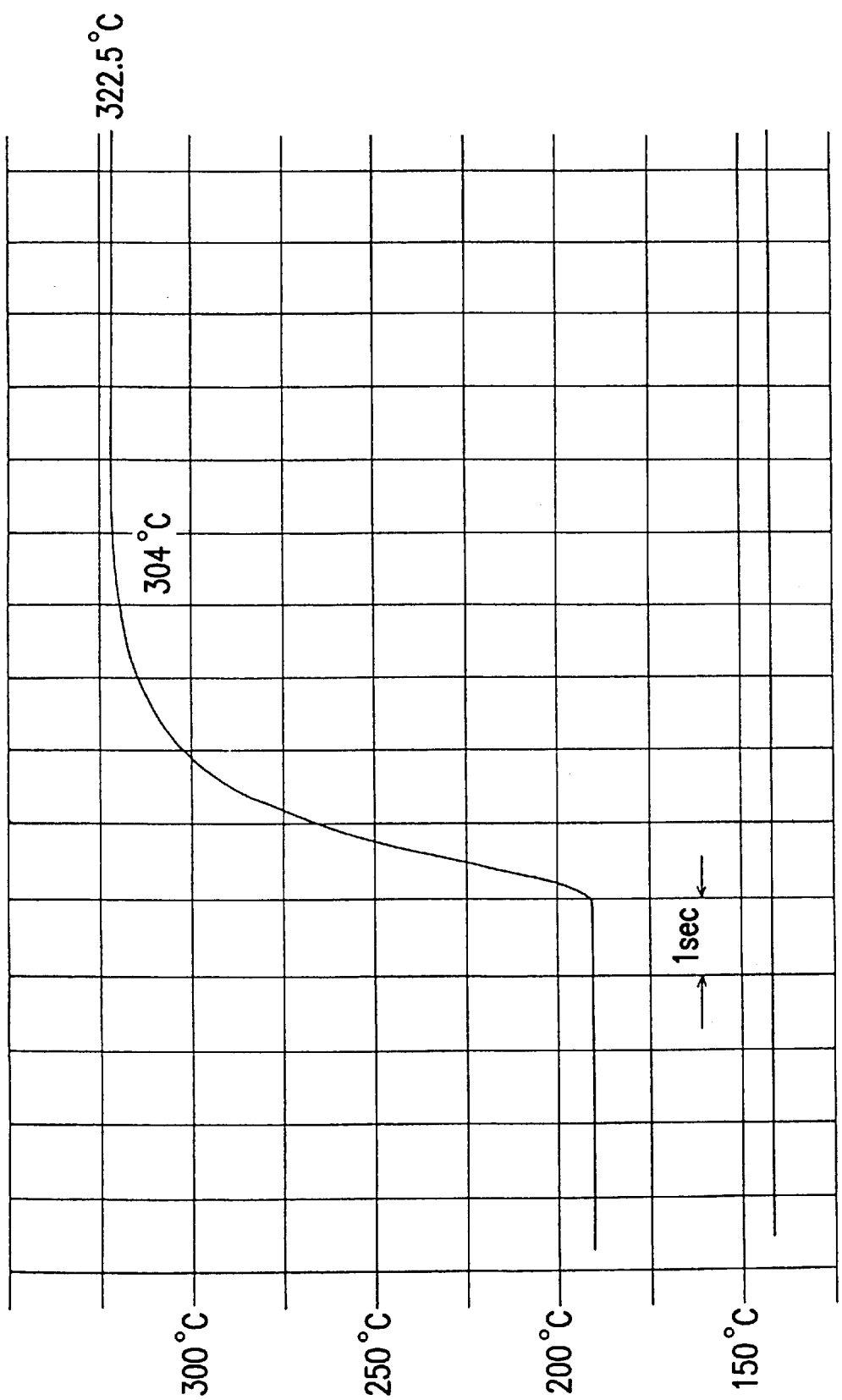
FIG. 9 is an example response characteristic of the detection sensor of the present invention.
Figure 10:
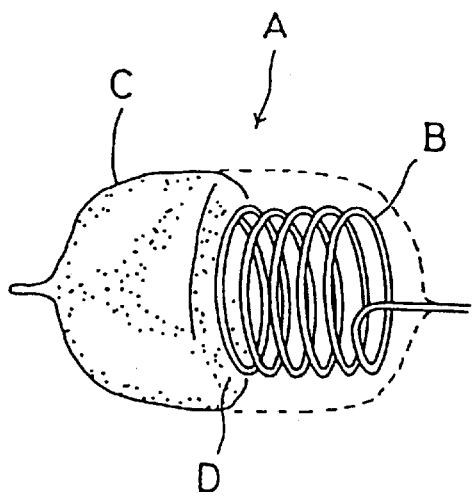
FIG. 10 is a partially broken away view of an example of the sensor element of the prior art contact catalytic reaction type sensor.
Figure 11:
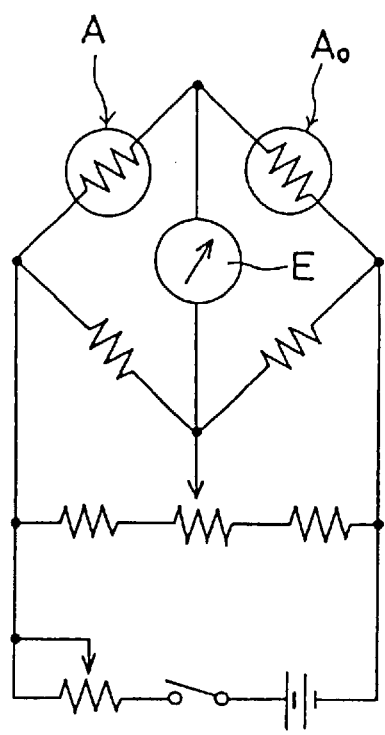
FIG. 11 is a circuit diagram of a flammable gas detector in which the sensor element in FIG. 10 is applied.
Figure 12:
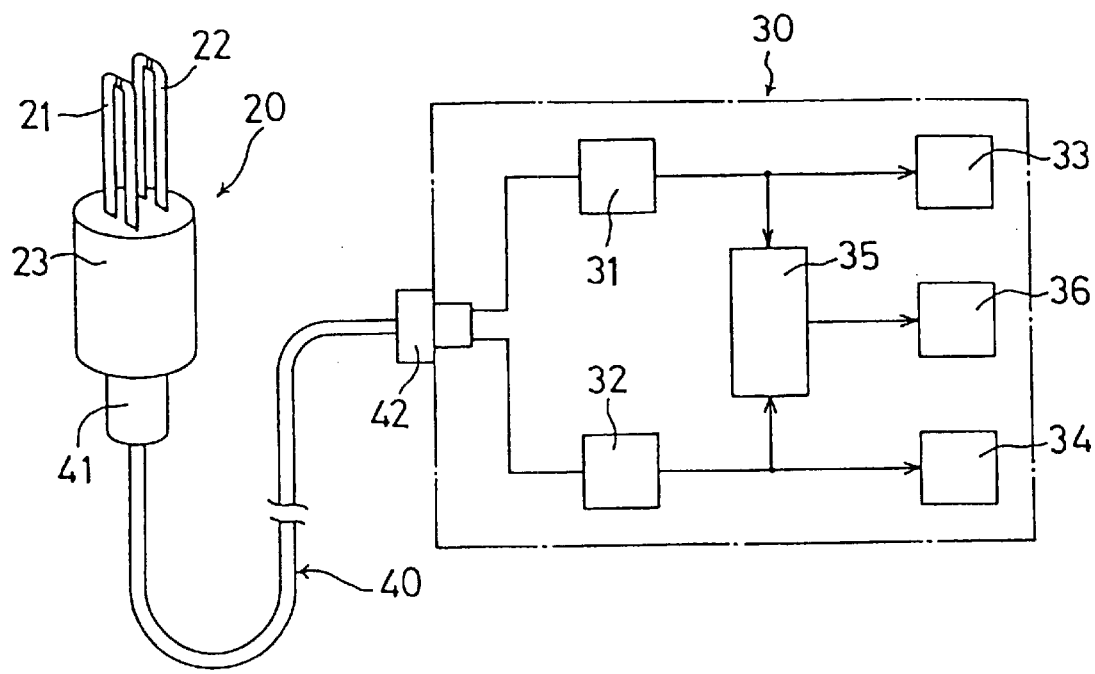
FIG. 12 illustrates a flammable gas detector as previously disclosed by the inventors.
Figure 13:
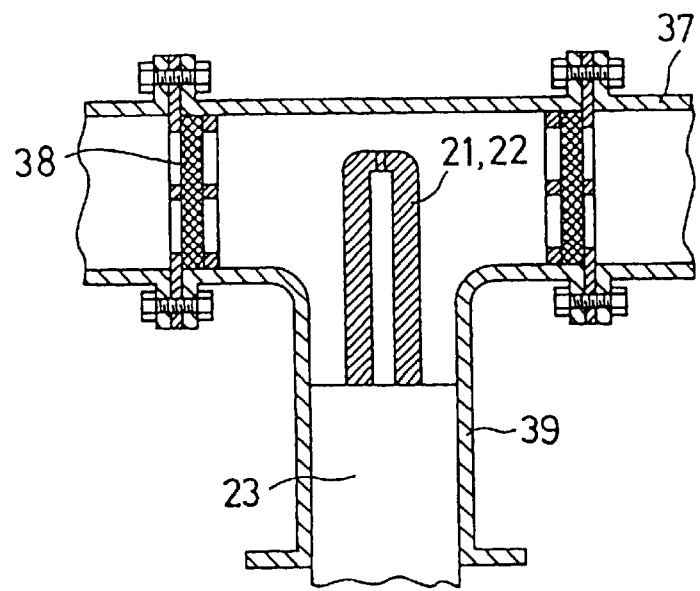
FIG. 13 is a schematic sectional view showing the mounting of the flammable gas detector illustrated in FIG. 12.

FIG. 9 shows the results of a response characteristic or responsiveness test of the flammable gas detector 1. The graph is actual measurements showing changes in temperature detection outputs of the two sensors 5, 6 when the $H_2$ concentration in the detection gas G was suddenly raised from 1.0% to 4.0%. The detection gas G was $N_2$ (800 SCCM)+$O_2$ (200 SCCM) (gas temperature 140° C.) and measurements were taken using the same first and second detection sensors 5, 6 as in the first and second examples.

As shown in FIG. 9, the temperature output (about 190.4° C.) of the first detection sensor 5, with the $H_2$ concentration of 1%, goes up to 304.25° C. in some 2.3 seconds.

When the concentration of $H_2$ was suddenly raised from 1% to 3.0%, 2.0% and 1.5% under the same conditions, it was 2.4 seconds, 2.6 seconds and 3.0 seconds respectively before the temperature detection outputs of the first detection sensor 5 reached 90% of the final temperature.

As is clear from FIG. 9, when the concentration of $H_2$ suddenly rises, the sudden increase in the gas concentration can be detected 2 to 3 seconds after that (i.e. with the time lag of 2 to 3 seconds). Thus, it is confirmed that the flammable gas detection sensor 2 is high in response characteristic.

In the experiments shown in FIGS. 6 to 8, detection gases G containing $H_2$ and $O_2$ were used, and measurements of the concentrations of $H_2$ and $O_2$ were described. The detection sensor 2 according to the present invention so works that the flammable gas is activated and subjected to combustion when coming in contact with the platinum coat, thereby detecting any flammable gas, even CO. Naturally, the flammable gas is not limited to hydrogen gas.

Also, as evident from FIG. 8, needless to say, gas detection sensor according to the present invention can be used as sensor for detection of the concentration of oxygen gas in flammable gases.

(Effects of the invention)

A gas detection sensor according to the invention comprises a first detection sensor that includes a diaphragm having a platinum coat which comes in contact with the flowing detection gas and a thermocouple having the one ends of two different kinds of metals put close to each other and fixed on the reverse side of the diaphragm not coming in contact with the gas and a second detection sensor of the same construction but without a platinum coat. Therefore, the present invention provides a flammable gas detection sensor very simple in construction in which there exists a quite linear relation between the detection output and the flammable gas concentration. The flammable gas detector according to the present invention is also very useful in detecting such gases as hydrogen gas remaining in the moisture taken out from the reactor for generation of moisture for semiconductor manufacturing facilities.

Also, as sensor according to the invention is capable of detecting, with high precision, the concentration of oxygen gas in the detection gas G containing flammable gas and is useful in detecting such gases as oxygen gas remaining in the moisture taken out from the reactor for generation of moisture.

It is also noted that the diaphragms of the respective detection sensors are made of stainless steel with the diaphragm gas-contact surface coated with a barrier coat as of TiN. And it has been confirmed that the adhesion between stainless steel and the barrier coat is extremely strong and will undergo little change with time. In the gas detection sensor according to the present invention, the platinum coat maintains its stable catalytic activity for a long time with no fear of the platinum coat and the barrier coat peeling off. Thus, the gas detection sensor permits measurement with high precision of the concentration of gas for a long time with no possibility of contaminating the high-purity gas.

Furthermore, when two detection sensors are mounted within the sensor block, it is the barrier coat with a very strong adhesion provided on the diaphragm and a coating film layer made up of the barrier coat and a platinum coat that are exposed in the gas flow passage.

Thus, with no fear at all of the diaphragm 5b getting damaged by the flowing detection gas, the gas detection sensor permits reliable and high precision measurement of the concentration of gas for a long time. Besides, the gas detection sensor according to the present invention is very simple in construction, which substantially reduces the dead space within the detection sensor. That improves gas exchangeability.

As set forth above, the present invention is excellent in practicability.

What is claimed is:

1. A flammable gas detection sensor wherein heating of the sensor by contact catalytic reaction of a flowing flammable detection gas gives off a detection signal of the flammable gas, said flammable gas detection sensor comprising:

a first detection sensor including a diaphragm having a platinum coat on a side thereof with which the flowing flammable detection gas comes in contact and a thermocouple having respective ends of two different kinds of metals placed close to each other and fixed on a reverse side of the diaphragm not coming in contact with the flowing flammable detection gas and which is heated by contact catalytic reaction of the flowing flammable detection gas, and a second detection sensor including a diaphragm having a surface coming in contact with the flowing flammable detection gas and a thermocouple having respective ends of two different kinds of metals placed close to each other and fixed on a reverse side of the diaphragm not coming in contact with the flowing flammable detection gas and which detects the temperature of the flowing flammable detection gas.

2. A gas detection sensor for detection of oxygen gas present in flammable gases wherein the heating of the sensor by contact catalytic reaction of a flowing flammable detection gas gives off a detection signal of oxygen gas in the detection gas, said gas detection sensor comprising:

a first detection sensor including a diaphragm having a platinum coat on a side thereof with which the flowing flammable detection gas comes in contact and a thermocouple having respective ends of two different kinds of metals placed close to each other and fixed on a reverse side of the diaphragm not coming in contact with the flowing flammable detection gas and which is heated by the contact catalytic reaction of the flowing flammable detection gas, and a second detection sensor including a diaphragm having a surface coming in contact with the flowing flammable detection gas and a thermocouple having respective ends of two different kinds of metals placed close to each other and fixed on a reverse side of the diaphragm not coming in contact with the flowing flammable detection gas and which detects the temperature of the flowing flammable detection gas.

3. A gas detection sensor as defined in claim 1 wherein the diaphragms of the first detection sensor and the second detection sensor are made of stainless steel and have a barrier coat coated on the surfaces of said respective diaphragms contacted by said flowing flammable detection gas.

4. A gas detection sensor as defined in claim 3 wherein the barrier coat is a barrier coat made of oxide or nitride.

5. A gas detection sensor as defined in claim 1 wherein the respective thermocouples are thermocouples made of chromel and alumel.

6. A gas detection sensor as defined in claim 1 wherein a stainless steel sensor block is provided with an inlet and an outlet for the flowing flammable detection gas, a gas flow passage through which the inlet and outlet communicate with each other, and first and second detection sensor insertion ports communicating with the gas flow passage, wherein the first detection sensor and the second detection sensor are fit into the first and second detection sensor insertion ports, respectively, provided in the stainless steel sensor block, with the surfaces of their respective diaphragms contacted by said flowing flammable detection gas faced with the gas flowing passage, in such a way that the respective detection sensor insertion ports are sealed airtight with said inserted diaphragms.

7. A gas detection sensor as defined in claim 2 wherein the diaphragms of the first detection sensor and the second detection sensor are made of stainless steel and have a barrier coat coated on the surfaces of said respective diaphragms contacted by said flowing flammable detection gas.

8. A gas detection sensor as defined in claim 7 wherein the barrier coat is a barrier coat made of oxide or nitride.

9. A gas detection sensor as defined in claim 2 wherein the respective thermocouples are thermocouples made of chromel and alumel.

10. A gas detection sensor as defined in claim 2 wherein a stainless steel sensor block is provided with an inlet and an outlet for the flowing flammable detection gas, a gas flow passage through which the inlet and outlet communicate with each other, and first and second detection sensor insertion ports communicating with the gas flow passage, wherein the first detection sensor and the second detection sensor are fit into the first and second detection sensor insertion ports, respectively, provided in the stainless steel sensor block, with the surfaces of their respective diaphragms contacted by said flowing flammable detection gas faced with the gas flowing passage, in such a way that the respective detection sensor insertion ports are sealed airtight with said inserted diaphragms.

* * * * *